United States Patent
Kantor et al.

(10) Patent No.: US 10,668,255 B2
(45) Date of Patent: Jun. 2, 2020

(54) SHEATH FOR MEDICALLY EXPANDABLE BALLOON

(71) Applicant: Medtronic Vascular, Inc., Santa Rosa, CA (US)

(72) Inventors: John Kantor, Healdsburg, CA (US); Claudio Silvestro, Healdsburg, CA (US); Shashank Raina, San Rafael, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 142 days.

(21) Appl. No.: 15/875,372

(22) Filed: Jan. 19, 2018

(65) Prior Publication Data

US 2019/0224460 A1 Jul. 25, 2019

(51) Int. Cl.
*A61M 29/00* (2006.01)
*A61M 31/00* (2006.01)
*A61M 25/10* (2013.01)
*A61B 17/88* (2006.01)
*A61F 2/95* (2013.01)

(52) U.S. Cl.
CPC ......... *A61M 25/10* (2013.01); *A61B 17/8855* (2013.01); *A61F 2/95* (2013.01); *A61M 2025/1081* (2013.01)

(58) Field of Classification Search
CPC ........... A61F 2/95; A61F 2/958; A61M 25/10; A61M 2025/1081; A61M 25/104
See application file for complete search history.

(56) References Cited

U.S. PATENT DOCUMENTS

| | | | |
|---|---|---|---|
| 5,188,605 A | 2/1993 | Sleep | |
| 5,383,928 A * | 1/1995 | Scott | A61F 2/07 623/1.12 |
| 5,647,857 A | 7/1997 | Anderson et al. | |
| 5,752,937 A | 5/1998 | Otten et al. | |
| 5,868,719 A | 2/1999 | Tsukernik | |
| 5,964,730 A | 10/1999 | Williams et al. | |
| 6,110,146 A | 8/2000 | Berthiaume et al. | |
| 6,592,548 B2 | 7/2003 | Jayaraman | |
| 7,105,013 B2 | 9/2006 | Durcan | |
| 8,414,528 B2 | 4/2013 | Liu et al. | |
| 8,852,257 B2 | 10/2014 | Liu et al. | |

(Continued)

OTHER PUBLICATIONS

Extended Search Report from counterpart European Application No. 19150997.5, dated Jun. 25, 2019, 6 pp.

(Continued)

*Primary Examiner* — Rebecca E Eisenberg
(74) *Attorney, Agent, or Firm* — Shumaker & Sieffert, P.A.

(57) ABSTRACT

A medical device includes a catheter, an expandable balloon on the distal portion of the catheter, and a sheath that is configured to enclose and protect the expandable balloon. The sheath extends within a sheath lumen of the catheter and out from the catheter through a distal opening of the sheath lumen. When in a deployed configuration, the sheath extends proximally to enclose at least a portion of the expandable balloon. The sheath may be axially movable within the sheath lumen of the catheter to actuate from the deployed configuration to a retracted configuration. In moving to the retracted configuration, the sheath may expose the outer surface of the expandable balloon.

31 Claims, 8 Drawing Sheets

(56) References Cited

U.S. PATENT DOCUMENTS

| | | |
|---|---|---|
| 9,072,590 B2 | 7/2015 | Wang et al. |
| 9,119,741 B2 | 9/2015 | Liu et al. |
| 2004/0093005 A1 | 5/2004 | Durcan |
| 2006/0015171 A1 | 1/2006 | Armstrong |
| 2006/0058866 A1 | 3/2006 | Cully et al. |
| 2009/0105686 A1* | 4/2009 | Snow .................. A61F 2/958 604/509 |
| 2010/0069852 A1* | 3/2010 | Kelley .................. A61F 2/95 604/264 |
| 2011/0184509 A1 | 7/2011 | Von Oepen et al. |
| 2011/0208284 A1 | 8/2011 | Hofmann et al. |
| 2011/0270226 A1 | 11/2011 | Kocur et al. |
| 2012/0296313 A1 | 11/2012 | Andreacchi et al. |
| 2013/0018309 A1 | 1/2013 | Ewing et al. |
| 2014/0343593 A1 | 11/2014 | Chin et al. |
| 2014/0379065 A1 | 12/2014 | Johnson et al. |
| 2015/0088241 A1 | 3/2015 | Liu et al. |
| 2015/0190618 A1 | 7/2015 | Kantor |
| 2015/0328028 A1 | 11/2015 | Wang et al. |
| 2016/0058983 A1 | 3/2016 | Poker et al. |
| 2018/0043138 A1 | 2/2018 | Chu |

OTHER PUBLICATIONS

U.S. Appl. No. 15/875,356, filed by Alan Connors et al., filed Jan. 19, 2018.
U.S. Appl. No. 15/875,343, filed by John Wilson Traxler et al., filed Jan. 19, 2018.
U.S. Appl. No. 15/875,331, filed Jan. 19, 2018, naming inventor Chiara Pedroni.
U.S. Appl. No. 15/875,318, filed Jan. 19, 2018, naming inventor Massimo et al.

* cited by examiner

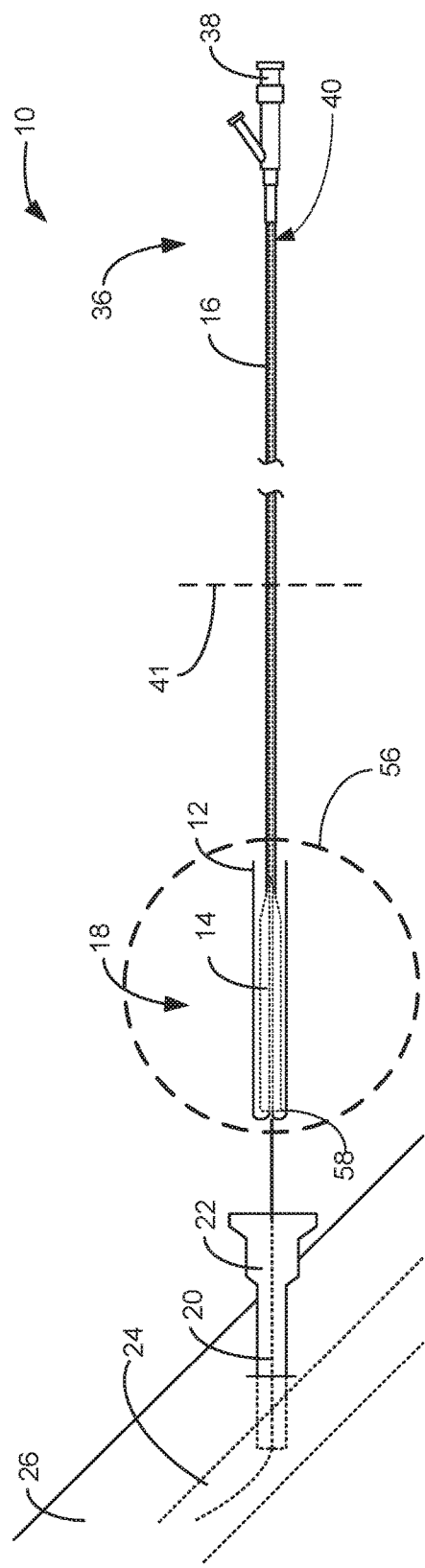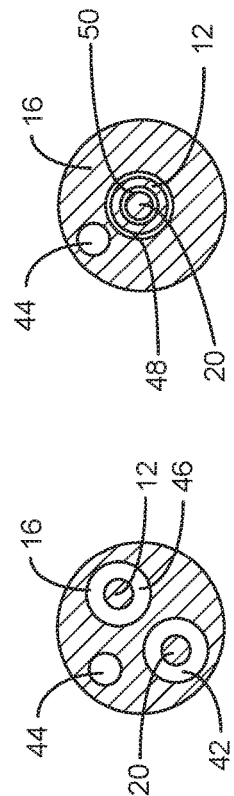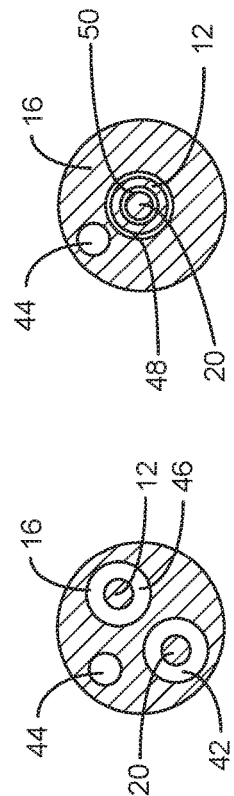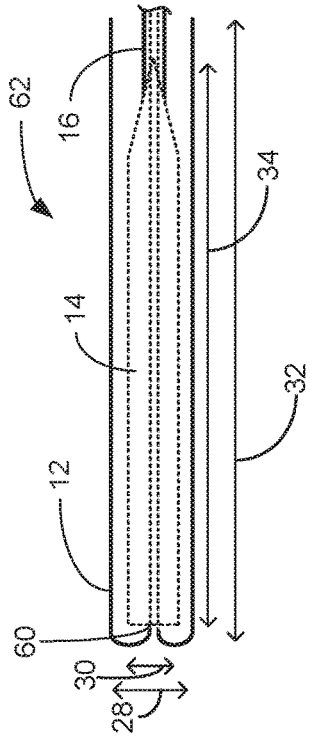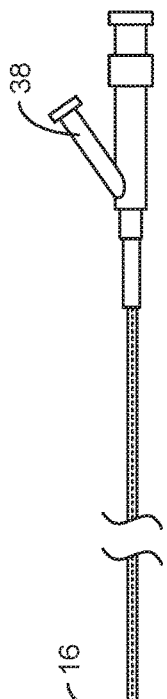

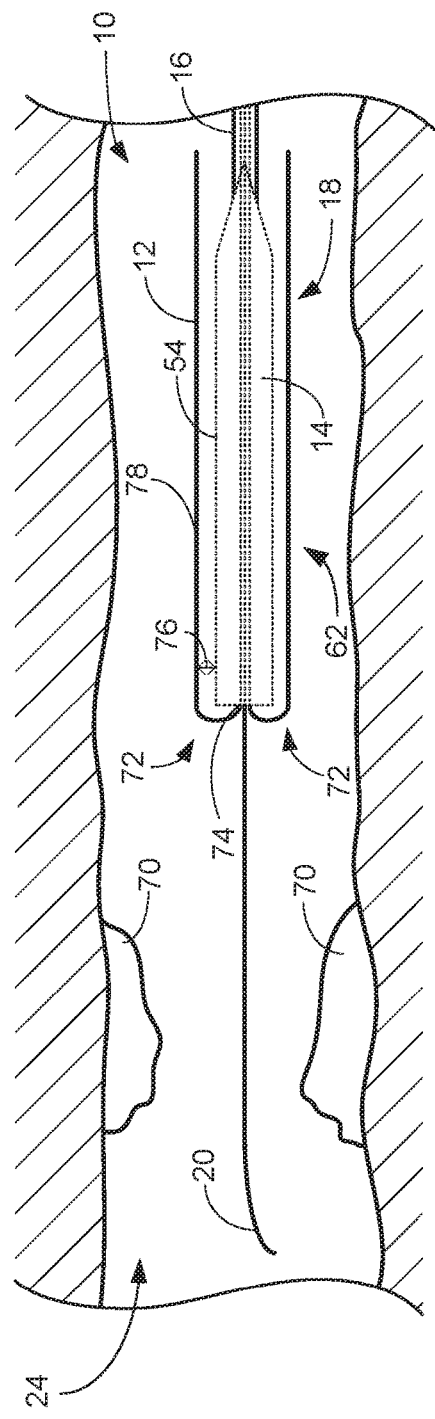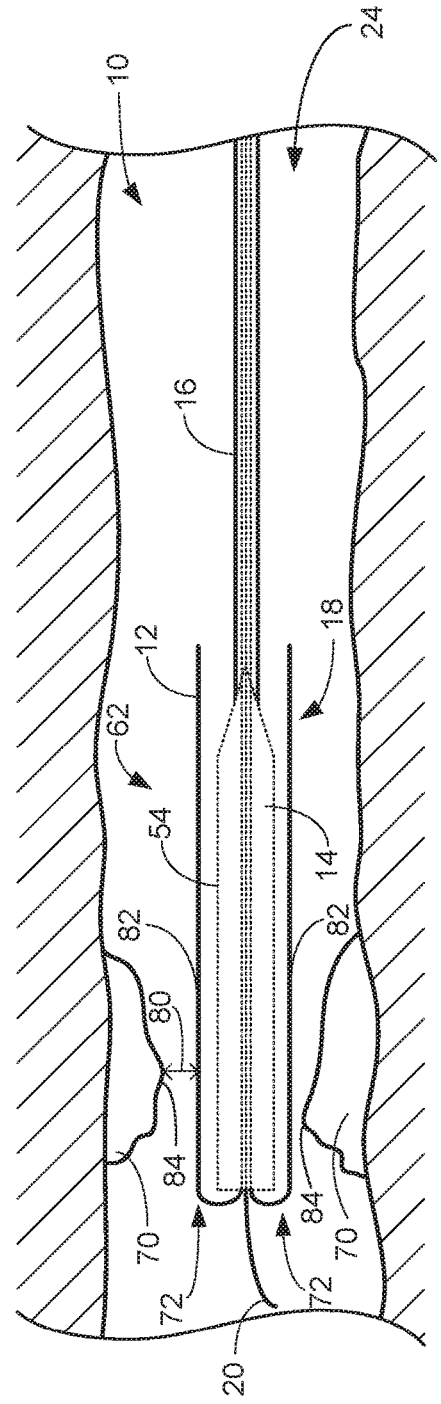

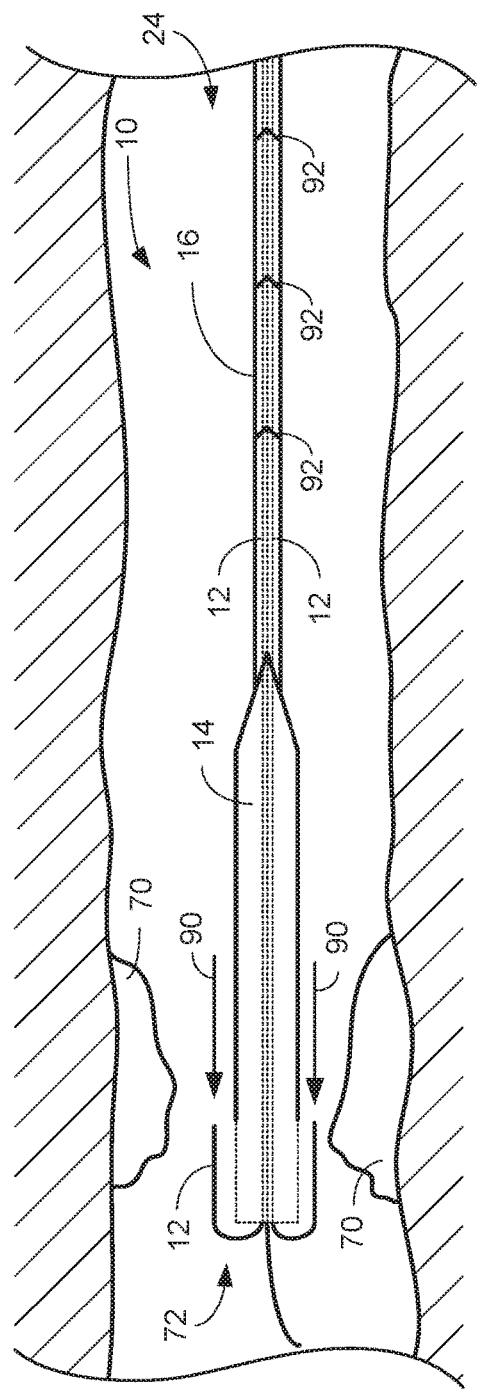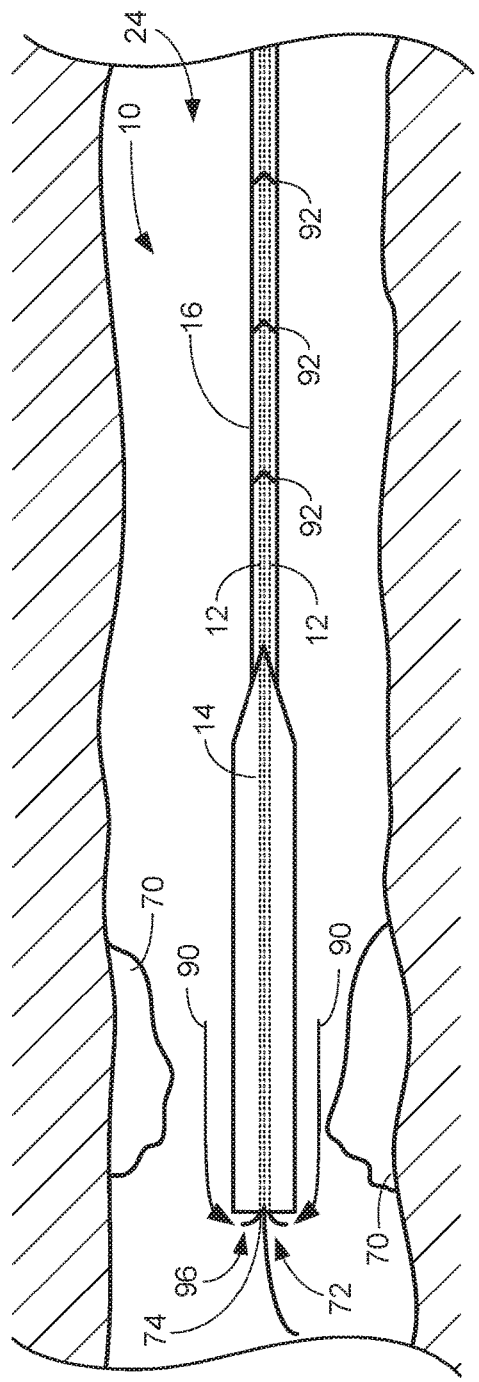

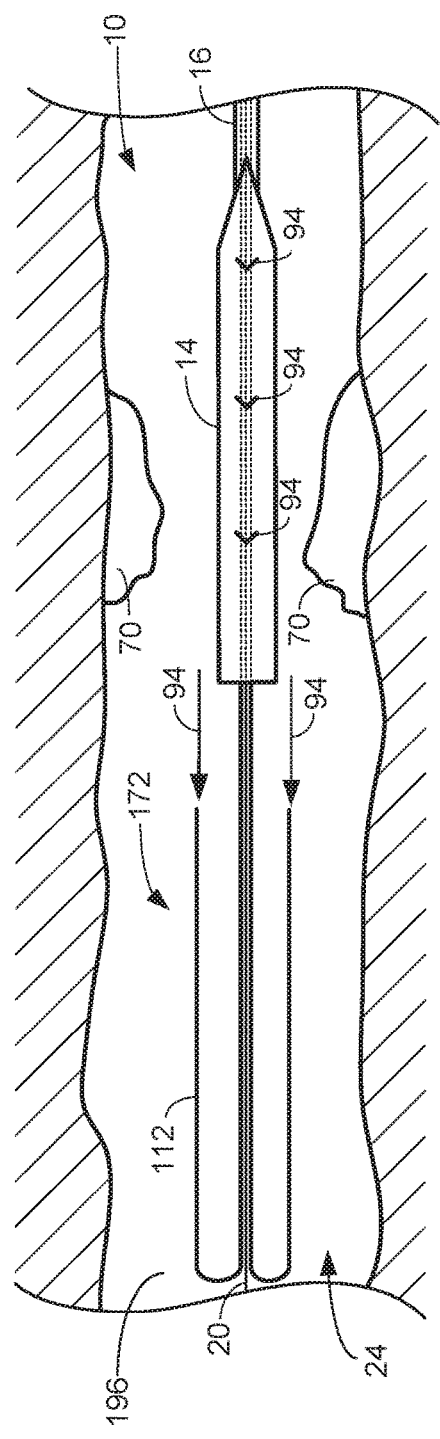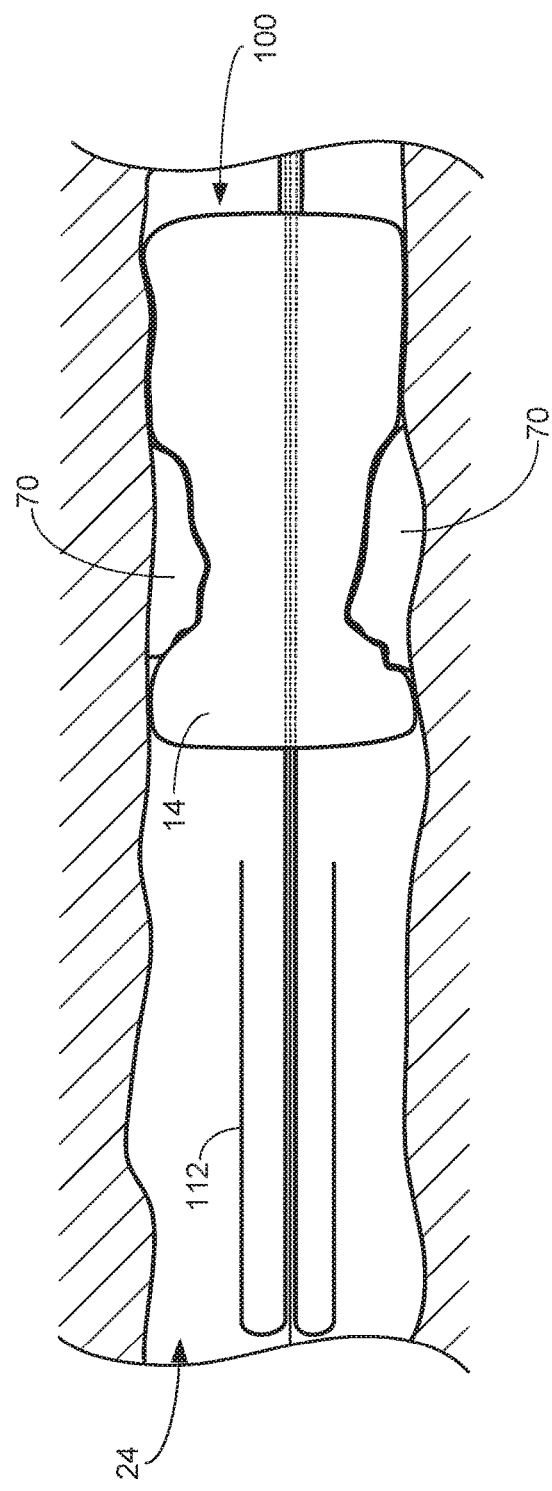

SHEATH FOR MEDICALLY EXPANDABLE BALLOON

TECHNICAL FIELD

This disclosure relates to medical sheaths, and more specifically sheaths for medically expandable balloon catheters.

BACKGROUND

Some medical treatments include the use of an inflatable balloon. The expandable balloon may be inserted in a patient, such as the vasculature of a patient, and navigated to a target site to be treated within that patient. Some expandable balloons may be fragile, such that it is relatively easy for the expandable balloon to incur damage during the insertion process. Further, some expandable balloons include coatings, such as drug coatings, which may be damaged or lost during insertion and/or navigation to the target site.

SUMMARY

In some aspects, this disclosure describes a medical device for housing an expandable balloon. The medical device may include a catheter, an expandable balloon on the distal portion of the catheter, and a sheath that is configured to enclose and protect the expandable balloon. The sheath may extend within a sheath lumen of the catheter and out from the catheter at a distal opening of the sheath lumen. The sheath curves proximally to enclose at least a portion of an outer surface of the expandable balloon. The sheath may enclose the expandable balloon when the sheath is in a deployed configuration. The sheath may be axially movable within the sheath lumen of the catheter from the deployed configuration to a retracted configuration. In moving to the retracted configuration, the sheath may axially extend or retract and expose the outer surface of the expandable balloon. The sheath in the deployed configuration is configured to enclose at least a portion of the expandable balloon during shipment, pre-procedural handling, and navigation of the expandable balloon through a patient's vasculature to a target site. In some examples, the sheath is moved to the retracted configuration to expose the expandable balloon in response to the balloon successfully navigating to the target site.

In a first example, aspects of the disclosure relate to a medical device that includes a catheter with a catheter shaft that includes a proximal end and a distal end, where the catheter shaft defines a sheath lumen having a distal opening at or near the distal end of the catheter. The medical device also includes an expandable balloon mounted in a deflated state on a portion of the catheter proximate to the distal end of the catheter at a location proximal to the distal opening of the sheath lumen. The medical device also includes a sheath configured to move from a deployed configuration to a retracted configuration. In the deployed configuration the sheath extends from the distal opening of the sheath lumen past a distal end of the expandable balloon and proximally over an outer surface of the expandable balloon, and in the retracted configuration the sheath moves axially within the sheath lumen to expose the outer surface of the expandable balloon.

In a second example relating to the medical device of the first example, the sheath is configured to extend proximally over the outer surface of the expandable to a location proximal to the expandable balloon.

In a third example relating to the medical device of the first and second example, the sheath is configured to retract proximally within the sheath lumen to expose the outer surface of the expandable balloon.

In a fourth example relating to the medical device of the first and second example, the sheath is configured to move distally past the distal end of the expandable balloon to expose the expandable balloon.

In a fifth example relating to the medical device of any of the first through fourth examples, the sheath includes a hypotube.

In a sixth example relating to the medical device of any of the first through fifth examples, the sheath is configured to shield the outer surface of the expandable balloon from a vasculature of a patient as the expandable balloon is navigated to a target site in the patient.

In a seventh example relating to the medical device of the sixth example, the sheath is configured to be actuated from the deployed configuration to the retracted configuration after navigating the expandable balloon to the target site.

In an eighth example relating to the medical device of the sixth and seventh examples, the sheath is configured to shield the expandable balloon from the vasculature of the patient as the expandable balloon is removed proximally from the body of the patient.

In a ninth example relating to the medical device of any of the first through eighth examples, the catheter also includes an inflation lumen fluidly connected to an internal volume of the expandable balloon to enable inflation of the expandable balloon.

In a tenth example relating to the medical device of any of the first through ninth examples, the catheter also includes a guidewire lumen.

In an eleventh example relating to the medical device of the tenth example, the guidewire lumen is parallel with the sheath lumen.

In a twelfth example relating to the medical device of the tenth example, the guidewire lumen is coaxial with the sheath lumen.

In a thirteenth example relating to the medical device of any of the first through twelfth examples, the sheath extends distally from the distal opening.

In a fourteenth example relating to the medical device of any of the first through thirteenth examples, the sheath includes a distal portion that is configured to be flexible and a proximal portion that is configured to have a relatively high tensile strength.

In a fifteenth example relating to the medical device of any of the first through fourteenth examples, a distal portion of the sheath is configured to be secured to an external surface of the catheter proximal to the expandable balloon.

In a sixteenth example relating to the medical device of the fifteenth example, the distal portion of the sheath is configured to be detached from the external surface in response to the sheath being retracted proximally through the sheath lumen.

In a seventeenth example relating to the medical device of any of the first through sixteenth examples, an outer surface of the expandable balloon is coated with a drug.

In an eighteenth example relating to the medical device of any of the first through seventeenth examples, an outer surface of a distal portion of the sheath when in the deployed configuration is coated with a drug.

In a nineteenth example relating to the medical device of the eighteenth example, the expandable balloon is coated with the drug.

In a twentieth example relating to the medical device of the eighteenth example, the expandable balloon is coated with a different drug.

In a twenty-first example relating to the medical device of any of the first through twentieth examples, an outer surface of a distal portion of the sheath when in the deployed configuration is coated with a lubricious coating.

In a twenty-second example relating to the medical device of any of the first through twenty-first examples, the sheath includes at least one of polytetrafluoroethylene, polyethylene, a biodegradable polymer, a flexible plastic blends or a thin-walled metal alloy.

In a twenty-third example, aspects of the disclosure relate to a method of deploying expandable balloons that includes navigating a distal portion of a catheter of a medical device through vasculature of a patient to a target site within the patient. The medical device includes a catheter with a catheter shaft that defines a sheath lumen, where the sheath lumen terminates distally with a distal opening at or near a distal end of the catheter. The medical device also includes an expandable balloon mounted in a deflated state on the distal portion of the catheter at a location proximal to the distal opening of the sheath lumen and a sheath. The sheath of the medical device is configured to move from a deployed configuration to a retracted configuration. In the deployed configuration, the sheath extends proximally from the distal opening of the sheath lumen to substantially cover the expandable balloon, and in the retracted configuration the sheath moves axially through the sheath lumen to expose the expandable balloon after navigating the distal portion of the catheter to the target site. The method of deploying expandable balloons also includes actuating the sheath axially through the sheath lumen to expose the expandable balloon to the vasculature of the patient.

In a twenty-fourth example relating to the method of the twenty-third example, the method includes retracting the distal portion of the catheter out of the vasculature of the patient and reinserting the distal portion of the catheter into the vasculature of the patient for navigation of the distal portion to the target site.

In a twenty-fifth example relating to the methods of the twenty-third and twenty-fourth examples, moving the sheath from the deployed configuration to the retracted configuration includes retracting the sheath proximally through the sheath lumen thereby moving the sheath distally from the balloon and then proximally within the sheath lumen.

In a twenty-sixth example relating to the method of the twenty-fifth example, retracting the sheath proximally through the sheath lumen includes proximally pulling on a proximal end of the sheath that extends out from a proximal hole at or near a proximal end of the catheter.

In a twenty-seventh example relating to the method of any of the twenty-third through twenty-sixth examples, moving the sheath from the deployed configuration to the retracted configuration also includes pushing the sheath distally through the sheath lumen thereby moving the sheath distally from the balloon.

In a twenty-eighth example relating to the method of the twenty-seventh example, pushing the sheath distally through the sheath lumen includes distally pushing a proximal end of the sheath that extends out from a proximal hole on a proximal end of the catheter.

In a twenty-ninth example relating to the method of any of the twenty-third through twenty-eighth examples, the method further includes inflating the expandable balloon through an inflation lumen to press drug-coated walls of the expandable balloon against the target site in response to actuating the sheath axially through the sheath lumen to expose the expandable balloon to the vasculature of the patient.

In a thirtieth example relating to the method of the twenty-ninth example, the method further including deflating the expandable balloon after a threshold period of time has elapsed since the drug-coated walls of the expandable balloon pressed against the target site as a result of inflating the expandable balloon.

In a thirty-first example relating to the method of the thirtieth example, the method also includes actuating the sheath axially through the sheath lumen to re-cover the expandable balloon subsequent to deflating the expandable balloon and retracting the catheter out of the vasculature of the patient.

In a thirty-second example, aspects of the disclosure relate to a medical device that includes a catheter with a catheter shaft that includes a guidewire lumen, an inflation lumen, and a sheath lumen that all extend throughout a length of the catheter, the sheath lumen terminating distally with a distal opening at or near a distal end of the catheter. The catheter is configured to follow a guidewire with the guidewire lumen sliding along the guidewire. The medical device also includes an expandable balloon mounted in a deflated state on the distal portion of the catheter at a location proximal to the distal opening of the sheath lumen, where the inflation lumen is configured to both inflate and deflate the expandable balloon. The medical device also includes a sheath configured to move from a deployed configuration wherein the sheath extends distally from the distal opening of the sheath lumen to extend proximally to substantially cover the expandable balloon, to a retracted configuration wherein the sheath moves axially within the sheath lumen to expose the outer surface of the drug-coated balloon.

The details of one or more examples are set forth in the accompanying drawings and the description below. Other features, objects, and advantages will be apparent from the description and drawings, and from the claims.

BRIEF DESCRIPTION OF THE DRAWINGS

FIG. 1A is a conceptual and schematic diagram illustrating a view of an example medical device including a sheath that encloses an expandable balloon on a catheter, and is shown near an example introducer sheath inserted in a body of a patient.

FIG. 1B is a conceptual and schematic diagram illustrating a detail view of the distal portion of the catheter of the medical device of FIG. 1A.

FIG. 1C is a conceptual and schematic diagram illustrating a view of the medical device of FIG. 1A without the sheath.

FIG. 2 is a conceptual and schematic diagram illustrating an example cross-sectional view of the catheter of FIG. 1A with a separate sheath lumen and guidewire lumen.

FIG. 3 is a conceptual and schematic diagram illustrating an example cross-sectional view of the catheter of FIG. 1A with a shared lumen for both the sheath and guidewire.

FIG. 4A is a conceptual and schematic diagram illustrating a view of an example expandable balloon being navigated to a target site within a body of a patient while enclosed within a sheath.

FIG. 4B is a conceptual and schematic diagram illustrating a view of the expandable balloon of FIG. 4A being navigated to a target site within a body of a patient while enclosed within a sheath.

FIG. 4C is a conceptual and schematic diagram illustrating a view of the sheath of FIG. 4A being retracted into the catheter of a medical device to expose the expandable balloon of FIG. 4A at the target site.

FIG. 4D is a conceptual and schematic diagram illustrating a view of the sheath of FIG. 4A being further retracted into the catheter of the medical device of FIG. 4A to expose the expandable balloon of FIG. 4A at the target site.

FIG. 5A is a conceptual and schematic diagram illustrating a view of an example sheath being actuated distally past the catheter of a medical device to expose an expandable balloon at a target site.

FIG. 5B is a conceptual and schematic diagram illustrating a view of the expandable balloon of FIG. 5A in an example inflated state at the target site.

DETAILED DESCRIPTION

Figure 6:
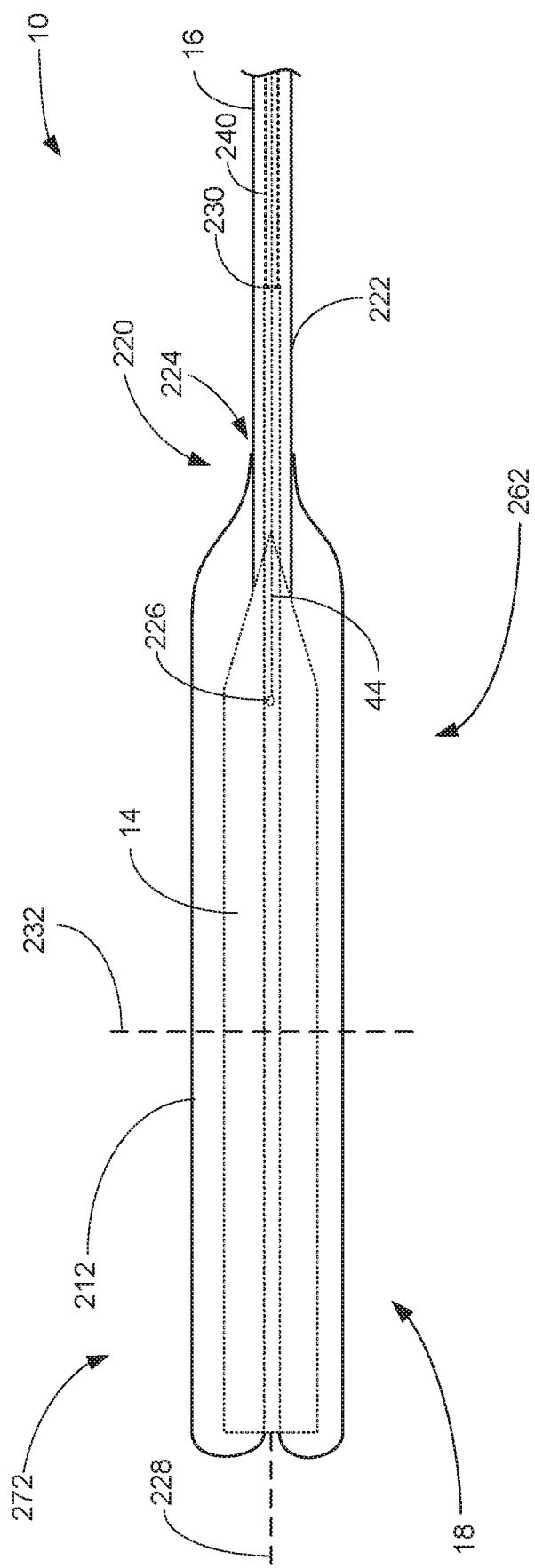
FIG. 6 is a conceptual and schematic diagram illustrating a side view of another example sheath enclosing an expandable balloon at the distal portion of a medical device, in which the distal end of the sheath is attached to a catheter at a location proximal to the expandable balloon.

In general, this disclosure describes an example medical device that includes a catheter, an expandable balloon attached to a distal portion of the catheter, and a sheath that encloses the expandable balloon. A portion of the sheath may be within a sheath lumen of the catheter, and extending out from a distal opening of the sheath lumen in a deployed configuration. In the deployed configuration, the sheath encloses at least a portion of the expandable balloon, and may enclose the expandable balloon from the distal opening to a position proximal to the expandable balloon. The sheath is configurated to move axially to a retracted configuration that exposes the expandable balloon. The sheath in the deployed configuration may enclose an expandable balloon during packaging, storing, inserting, and/or navigating the expandable balloon in a body of a patient. For example, the sheath in the deployed configuration may enclose the expandable balloon during packaging, storing, insertion, and intra-vasculature navigation of the expandable balloon, moving to the retracted configuration to expose the expandable balloon once the expandable balloon is successfully navigated to a target site within a body of a patient.

Medical balloons (also referred to herein as expandable balloons) are used in a variety of medical procedures, such as angioplasty, tuboplasty, or pyeloplasty. In medical procedures, the expandable balloon may be attached to a catheter that is configured to navigate the expandable balloon to a target site. The target site may be a location within a patient's body where the procedure is performed. In some medical procedures, the expandable balloon may be navigated to the target site in a deflated state and be inflated at the target site as part of the medical procedure.

The expandable balloon may be relatively delicate, being prone to kinking or flexing in ways that damage the structural integrity of the expandable balloon. For example, if handled improperly, the expandable balloon may become stuck to itself or become stretched, such that upon being inflated the expandable balloon may not inflate evenly or in the intended shape, or may inflate with an undesired weakness (e.g., the weakness making the expandable balloon more susceptible to popping or breaking). The sheaths described herein may enclose and protect or shield the expandable balloon until, for example, the expandable balloon is ready to be inflated (e.g., upon navigating the expandable balloon to the target site). Further, enclosing the expandable balloon in the sheaths described herein reduces or substantially eliminate contact between the expandable balloon and a user such as a clinician that is manipulating the expandable balloon. This may reduce the likelihood of kinking, flexing, or otherwise damaging the expandable balloon.

In some examples, an outer surface of the expandable balloon may be coated with a drug, which is delivered to the target site upon expanding the expandable balloon. For example, the drug may be intended to stop a hyperproliferative response of an intima within the vasculature of a patient, or the expandable balloon may be treated with one or more active pharmaceutical ingredients (e.g., paclitaxel or sirolimus) that have anti-restenotic properties. Such drug coatings may have relatively low adhesion to the expandable balloon such that contact between the drug coating and other surfaces or structures may remove some drug coating from the outer surface of the expandable balloon. This may increase variability and/or unpredictability in an amount of drug delivered to the target site, both of which are undesirable. The sheaths described herein may reduce inadvertent removal of drug from the surface of a coated expandable balloon.

FIG. 1A is a conceptual and schematic diagram illustrating a view of an example medical device 10 including a sheath 12, an expandable balloon 14, and a catheter 16. The expandable balloon 14 may be attached to the catheter 16 adjacent to a distal end 58 of the catheter 16 on a distal portion 18 of the medical device 10. In some examples, the expandable balloon 14 is fixedly attached adjacent to the distal end 58 of the catheter 16, such that it is difficult or impossible to remove the expandable balloon 14 from the catheter 16 without damaging one or both of the expandable balloon 14 or the catheter 16. In other examples, the expandable balloon 14 is loosely or removably attached to the catheter 16, such that the expandable balloon 14 may be detached from the catheter 16 once the expandable balloon 14 is navigated to the target site.

In some examples, the system in which the medical device 10 is utilized may include an introducer sheath 22. The introducer sheath 22 may be inserted in the patient transcutaneously in order to access vasculature 24 of a patient 26. An internal diameter of the introducer sheath 22 may be selected to accommodate an external diameter of the sheath 12 and an external diameter of the catheter 16.

The vasculature 24 of the patient 26 in which the introducer sheath 22 is inserted may be selected to provide access to a selected target site to which the expandable balloon 14 will be advanced. For example, the expandable balloon 14 may be used to provide anti-restenotic therapy to a target site in peripheral vasculature 24 of a patient 26.

The catheter 16 extends from a proximal end 36 adjacent to a hub 38, such as a manifold, to the distal end 58. The expandable balloon 14 is connected to the catheter 16 on the distal portion 18 of the medical device 10. The expandable balloon 14 may be connected to the catheter 16 adjacent to the distal end 58 of the catheter 16. The catheter 16 may include structural features that enable expansion or inflation of the expandable balloon 14 and advancing of the expandable balloon 14 to the target site in the patient 26. For example, the catheter 16 may include a guidewire lumen 42 and an inflation lumen 44 (see FIGS. 2 and 3). The catheter 16 may be configured to be navigate to a target site using a guidewire 20. The guidewire 20 may be a wire which was previously (e.g., previous to the catheter 16 being inserted) navigated to the target site within the vasculature 24 of a patient 26. A user (e.g., a clinician) may navigate the catheter 16 to a target site by sliding the catheter 16 along (e.g., advancing the catheter 16 over) the guidewire 20. A distal opening on the catheter 16 may initially receive the guidewire 20 outside of a patient 26, such that the catheter 16 advances along the guidewire 20 through the introducer sheath 22 into the vasculature 24 of the patient 26.

FIG. 1B is a conceptual and schematic diagram illustrating a detail view 56 of the distal portion 18 of the medical device 10 of FIG. 1A. The sheath 12 may be made of a number of suitable materials, such as poly(tetrafluoroethylene) (PTFE), high density polyethylene (HDPE), or low-density polyethylene (LDPE). As depicted in FIG. 1B, the sheath 12 is configured to enclose at least a portion of the expandable balloon 14 when the sheath 12 is in the deployed configuration 62. For example, the sheath 12 in the deployed configuration 62 may be configured to enclose the expandable balloon 14 as the expandable balloon 14 is navigated to the target site within a patient 26. When the sheath 12 is in the deployed configuration 62 while no external forces are applied to the sheath 12, the sheath 12 may substantially cover the expandable balloon 14 with little or no contact with the expandable balloon 14. For example, an internal diameter 28 of the sheath 12 may be greater than an external diameter 30 of the expandable balloon 14 when not in use. For example, the internal diameter 28 of the sheath 12 may be more than 1.0 millimeters greater than the external diameter 30 of the expandable balloon. In some configurations, during use, external forces applied to the sheath 12, such as compression forces from the introducer sheath 22 or the vasculature 24, may cause the sheath 12 to contact the expandable balloon 14. Further, a longitudinal length 32 of the portion of the sheath 12 that extends external to the catheter 16 may be greater than a longitudinal length 34 of the expandable balloon 14.

Configuring the sheath 12 in the deployed configuration 62 to enclose the expandable balloon 14 through the process of insertion reduces the likelihood of manual handling of the expandable balloon 14 by a user such as a clinician. Reducing the likelihood of manual handling of the expandable balloon 14 reduces a chance of physically damaging the expandable balloon 14, inadvertently removing portions of a drug coating from the expandable balloon 14, or both due to contact with a user such as a clinician or a structure external to the patient 26. Further, configuring the sheath 12 in the deployed configuration 62 to enclose the expandable balloon 14 as the expandable balloon 14 navigates the vasculature 24 of a patient 26 reduces or eliminates contact of the expandable balloon 14 with walls of the vasculature 24 during intravascular transit. Reducing the possibility of the expandable balloon 14 contacting walls of the vasculature 24 during intravascular transit may reduce or eliminate unintentional removal of a drug coating, physical damage to the expandable balloon 14, or both prior to the expandable balloon 14 reaching the target site.

Alternatively, rather than being configured to substantially avoid contact with the expandable balloon 14, the sheath 12 in the deployed configuration 62 may be configured to contact the expandable balloon 14. In some examples, this may result in the sheath 12 "resting" against the expandable balloon 14 such that the sheath 12 is configured to avoid applying a substantial inward radial force on the expandable balloon 14 when in the deployed configuration 62. For example, the internal diameter 28 of the sheath 12 may be substantially the same as or nominally greater than the external diameter 30 of the expandable balloon 14 when the expandable balloon 14 is in a deflated state and the sheath 12 is in the deployed configuration 62. For example, the internal diameter 28 of the sheath 12 may be 0.1-1.0 millimeters, more preferably 0.1-0.5 millimeters, greater than the external diameter 30 of the expandable balloon. Configuring the sheath 12 to nominally contact the expandable balloon 14 when the sheath 12 is in the deployed configuration 62 may reduce the size of the profile of the distal portion 18 of the medical device 10, potentially enabling the expandable balloon 14 to be navigated through relatively more tortuous or narrow vasculature 24. Further, the sheath 12 may be configured to move to a retracted configuration to expose the expandable balloon 14 without applying a substantial inward radial force to the expandable balloon 14. Configuring the sheath 12 to move from the deployed configuration 62 to a retracted configuration to expose the expandable balloon 14 without applying a substantial inward radial force to the expandable balloon 14 may decrease the chances of damaging the expandable balloon 14, damaging a drug coating on the expandable balloon 14, or both, as a substantial inward radial force may increase a chance of structurally damaging the expandable balloon 14, removing a drug coating from the expandable balloon 14, or both.

The sheath 12 may extend axially from the proximal end 36 of the catheter 16 to the distal end 58 of the catheter 16 within a sheath lumen 46 of the catheter 16 (see FIG. 2). In some examples, the sheath 12 may extend within the catheter 16 back to the hub 38 of the medical device 10. Configuring the medical device 10 such that the majority of the sheath 12 is transported within the catheter 16 may provide vasculature 24 navigation benefits by minimizing the profile of the distal portion 18 of the medical device 10. Put differently, where a medical device 10 utilizes the sheath 12 for protecting the expandable balloon 14 as described herein, configuring the medical device 10 such that some of the sheath 12 is housed within a lumen 46 of a catheter 16 of the medical device 10 may reduce a profile of the distal portion 18 of the medical device 10 (e.g., as a result of the lumen 46 of the catheter 16 being configured to compress the housed portion of the sheath 12 relatively more than the sheath 12 would be compressed if it were located external to the catheter 16).

The sheath 12 may extend distally from a distal opening 60 of the sheath lumen 46. The distal opening 60 may be on or adjacent to the distal end 58 of the catheter 16. The sheath 12 in the deployed configuration 62 extends from the distal opening to enclose at least a portion of the expandable balloon 14. The sheath 12 extends from the distal opening 60 to a location distal to the expandable balloon 14. The sheath 12 then extends radially outward to a radial distance greater than an outer radius of the expandable balloon 14, and extends proximally to enclose at least a portion of the expandable balloon 14 in the deployed configuration 62.

The sheath 12 in the deployed configuration 62 may be configured to enclose the expandable balloon 14 until the expandable balloon 14 is navigated to a target site within the vasculature 24 of a patient 26. As discussed herein, upon being navigated to the target site, the sheath 12 is configured to be axially moved from the deployed configuration 62 to the retracted configuration to expose the expandable balloon 14. Axial movement may be primarily proximal, primarily distal, or a combination of proximal and distal movement, as explained further below with respect to, for example, FIGS. 4C and 4D and FIGS. 5A and 5B. In other examples, the sheath 12 in the deployed configuration 62 may be configured to enclose the expandable balloon 14 until the expandable balloon 14 is inserted into the introducer sheath 22. In still other examples, the sheath 12 in the deployed configuration 62 may be configured to enclose the expandable balloon 14 until the expandable balloon 14 is brought into contact with the introducer sheath 22.

In some examples, an axial force may be applied to a proximal portion 40 of the sheath 12 (or an elongate member to which the proximal portion 40 of the sheath 12 is attached) to move/actuate the sheath 12 to the retracted configuration and expose the expandable balloon 14. For example, the proximal portion 40 may be configured to partially extend through a port of the hub 38, enabling a clinician to apply the axial force. In some examples, the proximal portion 40 of the sheath 12 may possess a relatively high tensile strength to transfer axial forces throughout the catheter 16. For example, the proximal portion 40 of the sheath 12 may include a hypotube that is attached to a distal portion of the sheath 12, wherein the distal portion of the sheath 12 is the portion of the sheath 12 that is sized and configured to extend over the expandable balloon 14.

In some examples, the sheath 12 may be configured to be actuated proximally through the catheter 16 to actuate the sheath 12 to the retracted configuration and expose the expandable balloon 14, such that the distal portion of the sheath 12 is pulled back into the catheter 16 to expose the expandable balloon 14 (see, for example, FIGS. 4C and 4D, described further below). In other examples, the sheath 12 may be configured to be actuated distally through the catheter 16 to actuate the sheath 12 to the retracted configuration and expose the expandable balloon 14, such that the distal portion of the sheath 12 is pushed distally past a distal end of the expandable balloon 14 within the vasculature 24 of the patient 26 (see, for example, FIGS. 5A and 5B, described further below). The sheath 12 may be configured to avoid pressing into the expandable balloon 14 during transportation and exposure of the expandable balloon 14. Configuring the sheath 12 to actuate to the retracted configuration without applying a substantial inward radial force, as described above, upon the expandable balloon 14 may increase the integrity of both the expandable balloon 14 and any drug coating on the expandable balloon 14.

The catheter 16 includes a set of axially extending lumens to facilitate inflation or expansion of the expandable balloon 14, actuation of the sheath 12, and advancement of the catheter 16 over the guidewire 20. FIG. 2 is an example cross-sectional view of the catheter 16 taken along the cross-sectional cut plane 41 in FIG. 1A. As depicted in FIG. 2, the catheter 16 includes a guidewire lumen 42, an inflation lumen 44, and a sheath lumen 46. The guidewire lumen 42 is configured to receive the guidewire 20. In some examples, the guidewire lumen 42 may extend longitudinally through the catheter 16 from the distal end 58 to the hub 38. The hub 38 may include a first port that provides access to the guidewire lumen 42 to facilitate advancing the catheter 16 along the guidewire 20.

Similarly, the inflation lumen 44 may be configured to extend longitudinally through the catheter 16 from the hub 38 to the expandable balloon 14. The hub 38 may include a second port that provides access to the inflation lumen 44. The inflation lumen 44 terminates distally at an orifice to the interior of the expandable balloon 14. The inflation lumen 44 is configured to receive a fluid that is flowed into the inflation lumen 44 from the hub 38 to expand or inflate the expandable balloon 14 (e.g., once the expandable balloon 14 has been navigated to the target site).

Similarly, the sheath lumen 46 extends longitudinally through the catheter 16. The sheath lumen 46 may extend from the hub 38 to the distal opening 60 that is distal to the expandable balloon 14. The sheath lumen 46 is configured to receive the sheath 12. The sheath lumen 46 may be substantially parallel with the guidewire lumen 42. The sheath 12 is configured to be moved through the sheath lumen 46, whether proximally or distally. To facilitate such/movement, in some examples, walls of the sheath lumen 46 may be coated with a lubricious coating, such as HDPE, PTFE, a hydrophilic material, or the like. The sheath 12 may be configured to be actuated in response to a force applied to a proximal portion 40 of the sheath 12 at or adjacent to a proximal end 36 of the catheter 16. For example, the sheath 12 may extend proximally from the hub 38, such that sheath 12 may be pushed distally or pulled proximally to actuate the sheath 12 and therein expose the expandable balloon 14.

Alternatively, in some examples, the sheath lumen 46 is combined with the guidewire lumen 42 to create a shared lumen. For example, FIG. 3 is a conceptual and schematic diagram of another example catheter 16 illustrating a cross-sectional view of the catheter 16 taken along the cross-sectional cut plane 41 in FIG. 1A. The example catheter 16 of FIG. 3 includes a shared lumen 48. As depicted in FIG. 3, the guidewire 20 and sheath 12 are coaxially enclosed in a single shared lumen 48. The shared lumen 48 may extend longitudinally through the catheter 16 from the distal end 58 of the catheter 16 to the hub 38. In some examples, the shared lumen 48 distally terminates at the distal opening 60, such that both the guidewire 20 and sheath 12 may distally extend from the distal end 58 of the catheter 16 from the distal opening 60. The sheath 12 may be configured to surround the guidewire 20 within the shared lumen 48. In such a configuration, the sheath 12 defines a space 50 between itself and the guidewire 20 to enable the sheath 12 and guidewire 20 to move independently through the shared lumen 48. In some examples in which the sheath lumen 46 is combined with the guidewire lumen 42 to create a shared lumen 48, the inflation lumen 44 may be substantially similar to the inflation lumen 44 of FIG. 2.

FIG. 1C is a conceptual and schematic diagram illustrating a side view of the expandable balloon 14 as arranged on the catheter 16. As depicted in FIG. 1C, the expandable balloon 14 is in a deflated configuration 52, which includes the expandable balloon 14 being folded or pleated into a physically smaller profile than the profile of the expandable balloon 14 in an inflated configuration. It is to be understood that the general shape of the deflated configuration 52 in FIG. 1C is for illustration purposes only; other shapes and configurations of the expandable balloon 14 in a non-inflated (or deflated) configuration 52 are also possible. Further, as depicted in FIG. 1C, the guidewire 20 extends from a position distal to the expandable balloon 14 longitudinally through the catheter 16 to the hub 38. In some examples, the guidewire 20 is advanced through the vasculature 24 of a patient 26 during a previous step, such that the catheter 16 is advanced over the guidewire 20 using the guidewire lumen 42 (or a shared lumen 48) to navigate the expandable balloon 14 to the target site (e.g., using the Seldinger technique). During such a technique, the guidewire 20 may only extend as far proximally through the guidewire lumen 42 as the catheter 16 has been pushed distally along the guidewire 20.

The expandable balloon 14 may be formed from any suitable material that provides sufficient strength and flexibility for the pressures experienced by the expandable balloon 14 during the inflation procedure. The materials from which the expandable balloon 14 is formed may be biocompatible and compatible with an optional drug coating on the outer surface 54 of the expandable balloon 14. In some examples, materials from which the expandable balloon 14 is formed may include nylon, polyethylene terephthalate (PET), polyethylene (such as crosslinked polyethylene), polyurethane, polyvinyl chloride, silicone elastomer, or the like.

In some examples, the expandable balloon 14 may include a coating on an outer surface 54 of the expandable balloon. The coating may include, for example, a lubricious coating (either hydrophilic or hydrophobic), a drug coating, or the like. In some examples, the drug coating may include a drug selected to treat peripheral artery disease, such as an anti-restenotic or anti-proliferative drug. An example anti-proliferative drug is paclitaxel. In some examples, the drug coating may further include an excipient to facilitate release of the drug from the drug coating. Example excipients include urea, polysorbate, sorbitol, or the like.

FIG. 4A is a conceptual and schematic diagram illustrating a view of the distal portion 18 of the medical device 10 within the vasculature 24 of a patient 26. The distal portion 18 of the medical device 10 may navigate the vasculature 24 of a patient 26 after being inserted through an introducer sheath 22 as depicted in FIG. 1A. The medical device 10 may navigate the vasculature 24 by advancing over the guidewire 20 that was previously guided to the target site 70. The target site 70 is an area within the vasculature 24 of a patient 26 that can be medically treated with an expandable balloon 14. As depicted in FIG. 4A, the distal portion 18 of the medical device 10 is approaching the target site 70, which in this case is a raised lesion. Other examples of target sites 70 that may be treated with an expandable balloon 14 are also possible.

When in the deployed configuration 62, the distal portion 72 of the sheath 12 may extend distally from the catheter 16 to a location 74 distal to the expandable balloon 14. The distal portion 72 of the sheath 12 may include a section of the sheath 12 that extends radially outward with respect to the catheter 16 (e.g., extend out to enclose the expandable balloon 14). The expandable balloon 14 may completely encircle the distal end 58 of the catheter 16 (e.g., therein enclosing a portion of the catheter 16 adjacent to the distal end 58 of the catheter 16) while the sheath 12 may completely encircle the expandable balloon 14 when in the deployed configuration 62, enclosing the expandable balloon 14.

The sheath 12 may be made of a number of suitable materials, such as poly(tetrafluoroethylene) (PTFE), polyethylene (PE), high density polyethylene (HDPE), low density polyethylene (LDPE), or other flexible plastic blends or thin-walled metal alloys. In some examples, the sheath 12 is configured to be biodegradable. In some examples, the distal portion 72 of the sheath 12 is made from a flexible material which is bonded to a stiffer material of the proximal portion of the sheath 12 near the hub (neither of which are depicted in FIGS. 4A and 4B) to enable the axial retraction of the sheath 12. For example, the distal portion 72 of the sheath 12 may include a flexible material such as LDPE or another material described herein. The distal portion 72 of the sheath 12 extends proximally from the distal location 74 to enclose the expandable balloon 14. Further, a proximal portion of the sheath 12 may include a material with more tensile strength than the distal portion 72, such as a hypotube, that is attached to the distal portion 72. In other examples, rather than the distal portion 72 of the sheath 12 being a different material than the proximal portion 40 of the sheath 12, the proximal portion of the sheath 12 may be a substantially similar or identical material. In such examples, the proximal portion of the sheath 12 may define a greater wall thickness than the distal portion 72 of the sheath 12 (e.g., such that the proximal portion of the sheath 12 is twice as thick as the distal portion 72 of the sheath 12) to give the proximal portion of the sheath 12 more tensile strength and/or rigidity.

In some examples, the sheath 12 is configured to enclose the expandable balloon 14 in the deployed configuration 62 during navigation of the vasculature 24. The sheath 12 may be configured to avoid contacting the expandable balloon 14 while navigating to the target site 70 in the deployed configuration 62. For example, when in the deployed configuration 62 the sheath 12 may define a space 76 between an inner wall 78 of the sheath 12 and the outer surface 54 of the expandable balloon 14. The space 76 may be large enough to substantially eliminate contact between the sheath 12 and expandable balloon 14 prior to use (e.g., shipping, pre-procedural handling), and minimize contact between the sheath 12 and expandable balloon 14 during navigation of vasculature 24. In other examples, when in the deployed configuration 62 an inner wall 78 of the sheath 12 may nominally contact the outer surface 54 of the expandable balloon 14 without significantly pressing into the outer surface 54 of the expandable balloon 14. For example, the inner wall 78 of the sheath 12 may be configured to rest against or slide along the outer surface 54 of the expandable balloon 14 without applying a substantial inward radial force upon the expandable balloon 14 when the sheath 12 is in the deployed configuration 62. Configuring the sheath 12 to minimize or eliminate inward radial forces that are applied (e.g., applied by the sheath 12) to the outer surface 54 of the expandable balloon 14 when the sheath 12 is in the deployed configuration 62 during standard operations of the medical device 10 (e.g., 14 actuation of the sheath 12 to the retracted configuration, pre-procedural handling of the expandable balloon 14, inflation of the expandable balloon 14) may increase the structural integrity of the expandable balloon 14, drug coatings thereon, or both.

The inner wall 78 of the sheath 12 may be lubricious to reduce friction or force being transmitted or created between the inner wall 78 and the outer surface 54 of the expandable balloon 14. In some examples, the inner wall 78 may be treated with or otherwise receive a coating to configure the inner wall 78 to be lubricious, such as a hydrophilic coating, a PTFE coating, or a HDPE coating. For example, the majority of a distal portion 72 of the sheath 12 may be made of LDPE, while the inner wall 78 is coated with a hydrophilic coating, PTFE, or HDPE. Alternatively, the entirety of the distal portion 72 of the sheath 12 may be made of PTFE or HDPE. Configuring the inner wall 78 of the sheath 12 to be lubricious may reduce the likelihood of the sheath 12 physically damaging the expandable balloon 14, removing some of the drug coating on an outer surface 54 of the enclosed expandable balloon 14, or both.

FIG. 4B is a conceptual and schematic diagram illustrating the distal portion 18 of the medical device 10 at the target site 70. The distal portion 18 of the medical device 10 may arrive at the target site 70 after being inserted through the introducer sheath 22 as depicted in FIG. 1A and navigated through vasculature 24 of the patient 26 as depicted in FIG. 4A (e.g., over the guidewire 20). In some examples, as depicted, there is space 80 between an outer surface 82 of the sheath 12 and an inner wall 84 of the target site 70. However, the medical device 10 may be configured to navigate and deploy the expandable balloon 14 at target sites 70 where there is relatively little or substantially no space 80 between the outer surface 82 of the sheath 12 and the inner wall 84 of the target site 70.

In some examples, the outer surface 82 of the distal portion 72 of the sheath 12 is treated or coated with a material. For example, the outer surface 82 of the sheath 12 may be treated with a lubricious coating to enhance the navigability of the medical device 10 through the vasculature 24. The lubricious coating may be a hydrophilic or hydrophobic-based coating. The lubricious coating may facilitate navigation of the medical device 10 through a tortuous or relatively narrow vasculature 24 without damaging the integrity of the expandable balloon 14 or a drug coating thereon (e.g., as the static/dynamic friction may have otherwise applied forces upon the expandable balloon 14 through the sheath 12 if not for the lubricious coating).

In other examples, the outer surface 82 of the sheath 12 is treated with a drug, such as a drug for treating the target site 70. The sheath 12 may administer the drug while in the deployed configuration 62 upon the sheath 12 navigating to the target site 70. In some examples, the sheath 12 administers the drug to the target site 70 through the contact that occurs by navigating the expandable balloon 14 to the target site 70 and then moving/actuating to expose the expandable balloon 14. Alternatively, the sheath 12 may be configured to administer the drug to the target site 70 by being moved (e.g., twisted or shifted) to create contact between the outer surface 82 of the sheath 12 and the target site 70. In some examples, the entire distal portion 18 of the medical device 10 may be moved radially and/or longitudinally within the vasculature 26 to therein move the sheath 12 and administer the drug. In other examples, the sheath 12 may be configured to be independently moved to administer the drug to the target site 70 while the catheter 16 and expandable balloon 14 stay relatively stationary. For example, a clinician may apply a force to the proximal portion 40 of the sheath 12 that transmits the force axially through the catheter 12, eventually causing the sheath 12 to move radially outward and contact the target site 70 (e.g., as a result of the distal portion 72 splaying radially outwards when retracted/actuated into the catheter 16, or the expandable balloon 14 being inflated to a low-pressure state prior to the sheath 12 being actuated).

In some examples, both the outer surface 54 of the expandable balloon 14 and the sheath 12 may be coated with a drug. The sheath 12 may be coated with the same drug or a different drug than is on the outer surface 54 of the expandable balloon 14. Where both the outer surface 54 of the expandable balloon 14 and the outer surface 82 of the sheath 12 are coated with a substantially similar drug, the medical device 10 may have an increased ability to apply a single drug to the target site 70 (e.g., in comparison to just the expandable balloon 14 being coated with the drug), as more surface area is available to store the drug. For example, the sheath 12 may deliver a pre-dose of the drug to the target site 70, and thereafter the expandable balloon 14 compresses, for example, a lesion or stenosis while simultaneously delivering a therapeutically effective amount of the drug, such as paclitaxel.

Alternatively, where the outer surface 54 of the expandable balloon 14 is coated with a different drug than the outer surface 82 of the sheath 12, the medical device 10 may be configured to execute a two-step administration of the different drugs. A drug on the sheath 12 may have different pharmaceutical characteristics relative to the drug on the expandable balloon 14. For example, the drug on the sheath 12 may have different characteristics related to solubility, in-tissue transfer, lesion-inhibition, cellular uptake, and/or hydrophilic/hydrophobic properties in comparison to a drug on the outer surface 54 of the expandable balloon 14. This may enable a property of the drug on the sheath 12 to impact or improve a property of the drug on the expandable balloon 14. In some examples, a drug on the sheath 12 may improve the ability of a drug on the expandable balloon 14 to treat the target site 70.

For example, where a particularly small lesion is targeted, a small expandable balloon 14 may be used for treatment, such that the outer surface 54 of the small expandable balloon 14 only has sufficient room to host the desired dosage of a lesion-inhibition drug, therein enabling no room for an application of a cellular uptake drug. In such an example, the outer surface 82 of the sheath 12 may be treated with the cellular uptake drug. In this way, treating the outer surface 82 of the sheath 12 with a drug may improve the ability of the medical device 10 to hold and apply different drugs to a target site.

FIGS. 4C and 4D are conceptual and schematic diagrams illustrating the sheath 12 actuating to the retracted configuration 96 proximally through the catheter 16 to expose the expandable balloon 14 at the target site 70. The distal portion 72 of the sheath 12 is configured to retract in a distal direction 90 while the portion of the sheath 12 that is inside the catheter 16 retracts in a proximal direction 92. The sheath 12 is configured to be moved/actuated to the retracted configuration 96 in response to a proximal force that is applied to a proximal portion 40 of the sheath 12. A clinician may apply the proximal force to the proximal portion 40 of the sheath 12. The distal portion 72 of the sheath 12 retracts back into the catheter 16 through the distal opening 60. In this example configuration, the distal portion 72 of the sheath 12 is relatively flexible and thin so that it can be easily bend around and into the catheter 16 as it is retracted.

The distal portion 72 of the sheath 12 may be configured to retract substantially straight distally to the location 74 when actuating to the retracted configuration 96. In other examples, the distal portion 72 of the sheath 12 may angle radially outward in response to the proximal force as the distal portion 72 of the sheath 12 retracts to the retracted configuration 96. The sheath 12 may be configured to not exert substantial radially inward forces upon the expandable balloon 14 as the sheath 12 actuates to the retracted configuration 96.

Alternatively, in another example configuration, the sheath 12 may be configured to actuate distally to a retracted configuration 196, therein exposing the expandable balloon 14. For example, FIG. 5A is a conceptual and schematic diagram illustrating a sheath 112 actuating distally to a retracted configuration 196 to expose the expandable balloon 14 at the target site 70. A sheath 112 that is configured to actuate distally to the retracted configuration 196 may be substantially similar to a sheath 12 that is configured to retract proximally as described above, except as described herein. In some examples, a distal portion 172 of a sheath 112 that is configured to actuate distally to the retracted configuration 196 may be stiffer (e.g., may have a higher tensile strength and/or thickness) than a distal portion 72 of a sheath 12 that is configured to retract proximally to a retracted configuration 96. Providing more stiffness and tensile strength to a distal portion 172 of a sheath 112 that is configured to actuate distally may facilitate the distal portion 172 of the sheath 112 sufficiently pushing past the target site 70 within a vasculature while unsupported (e.g., unsupported by the catheter 16) to expose the expandable balloon 14.

Both the distal portion 172 of the sheath 112 and the portion of the sheath 112 that is inside the catheter 16 is configured to actuate to the retracted configuration 196 in a distal direction 90. The sheath 112 is configured to be actuated in response to a distal force that is applied to a proximal portion 40 of the sheath 112. A clinician may apply the distal force to a proximal portion 40 of the sheath 112 that is, for example, extending out from the hub 38. The distal portion 172 of the sheath 112 may be configured to substantially retain its shape (e.g., the shape the distal portion 172 of the sheath 112 had when navigating the vasculature 24 of the patient 26) as the distal portion 172 is distally actuated to the retracted configuration 196.

FIG. 5B is a conceptual and schematic diagram illustrating the expandable balloon 14 in the inflated state 100 at the target site 70. Though FIG. 5B shows the expandable balloon 14 in the inflated state 100 after being exposed by the sheath 112, it is to be understood that the expandable balloon 14 may expand in substantially the same manner if exposed by the sheath 12 of FIGS. 1A-4D.

The expandable balloon 14 is expanded using the inflation lumen 44. The expandable balloon 14 may be inflated to substantially fill the vasculature 24 around the target site 70. Any drug coating on the expandable balloon 14 may be administered to the target site 70 once the expandable balloon 14 is inflated to the inflated state 100. The expandable balloon 14 may be deflated (e.g., deflated using the inflation lumen 44) after a period of time has passed (e.g., a period of time sufficient to compress the lesion or stenosis; a period of time sufficient to administer any drug that is coated on the expandable balloon 14). In some examples, the sheath 112 (or sheath 12, in other examples) is actuated back to the deployed configuration 62 to re-envelope the expandable balloon 14. Alternatively, after the sheath 112 is actuated to the deployed configuration 62, the catheter 16 and expandable balloon 14 may be advanced (e.g., pushed distally) relative to the sheath 112 (e.g., as a result of a clinician holding the proximal portion of the sheath 112 stationary while distally advancing the catheter 16 and expandable balloon 14) until the sheath 112 has effectively recaptured the expandable balloon 14.

In some examples, the expandable balloon 14 may be configured to deflate to a different shape than the deflated configuration 52 which the expandable balloon 14 defined before the expandable balloon 14 was inflated. For example, the expandable balloon 14 may deflate to a shape/profile that is larger than the (initial) deflated configuration 52 following the inflation and subsequent deflation of the expandable balloon 14. In such examples, the sheath 112 (or sheath 12, in other examples) may be configured to press radially down upon the expandable balloon 14 to reduce the size of the shape/profile of the expandable balloon in response to the expandable balloon 14 being deflated. Configuring the sheath 112 (or sheath 12, in other examples) to radially compress the expandable balloon 14 following the inflation and deflation of the expandable balloon 14 may improve the ability of the distal portion 18 of the medical device 10 to retract from the vasculature 24 following the procedure.

In some examples, sheaths 12, 112 may be configured to be removably attached to a portion of the catheter 16 that is proximal to the expandable balloon 14. For example, FIG. 6 is a conceptual and schematic diagram illustrating an example sheath 212 that is enclosing an expandable balloon 14 on the distal portion 272 of a catheter 16 on a medical device 10. The sheath 212 may be substantially similar to the sheaths 12, 112 of FIGS. 1A-5B. The sheath 212 may extend proximally from the medical device 10 substantially parallel to a longitudinal axis 228 of the catheter 16 to enclose the expandable balloon 14. A distal end 220 of the sheath 212 is attached to an outer surface 222 of the catheter 16. The distal end 220 of the sheath 212 is attached to the catheter 16 at a location 224 proximal to the expandable balloon 14. In some examples, the distal end 220 of the sheath 212 is only attached to the outer surface 222 of the catheter 16 when the sheath 212 is in the deployed configuration 262. The distal end 220 of the sheath 212 may be attached with an adhesive, such as a glue or an adhesive strip, or a friction fit with a complementary structure of the catheter 16, or the like.

The distal end 220 may be relatively lightly attached to the outer surface 222 of the catheter 16, such that the distal end 220 is configured to detach from the catheter 16 without damaging the catheter 16 or sheath 12 in response to a relatively small axial force upon the distal end 220. In some examples, the distal end 220 is configured to detach from the catheter 16 in response to a force applied by a clinician to a proximal portion 240 of the sheath 212 to actuate the sheath 212 to the retracted configuration (e.g., retracted configurations 96, 196) to expose the expandable balloon 14 as discussed herein. The distal end 220 may be configured to remain attached during navigation of the vasculature 24 of a patient 26 to a target site 70. Attaching a distal end 220 of the sheath 212 to the catheter 16 may reduce the chances of the distal end 220 of the sheath 212 unintentionally sliding distally and therein prematurely expose some or all of the expandable balloon 14 as the expandable balloon 14 is navigated through the vasculature 24 of a patient 26. For example, if the distal portion 18 of the medical device 10 needs to be retracted (e.g., moved proximally) before deployment of the expandable balloon 14, attaching the distal end 220 of the sheath 212 to the catheter 16 may improve the ability of the sheath 212 to enclose the expandable balloon 14 during such proximal movement. Further, for expandable balloons 14 that are coated with a drug, attaching the distal end 220 of the sheath 212 to the catheter 16 will help reduce or eliminate an amount of blood that may come into contact with the expandable balloon 14 while navigating through the vasculature 24, thus protecting any drug coating from being washed off or otherwise removed as a result of such contact with blood.

The inflation lumen 44 may terminate at an orifice 226 to the expandable balloon 14. In some examples, the inflation lumen 44 may terminate at a plurality (not depicted) of orifices 226 to the internal volume of the expandable balloon 14. The orifice(s) 226 are configured to transfer fluid of the inflation lumen 44 into and out of the expandable balloon 14 to inflate and deflate the expandable balloon 14 to the inflated state 100 and deflated configuration 52, respectively.

In some examples, the distal portion 272 of the sheath 212 is connected to the proximal portion 240 of the sheath 12 at a junction 230. In some examples, the proximal portion 240 includes a flexible wire, metal hypotube, or a thin walled metal alloy. The distal portion 272 of the sheath 12 may be bonded (e.g., welded, glued) or mechanically connected (e.g., interlocked, fastened) at the junction 230 to the proximal portion 240.

Figure 7:
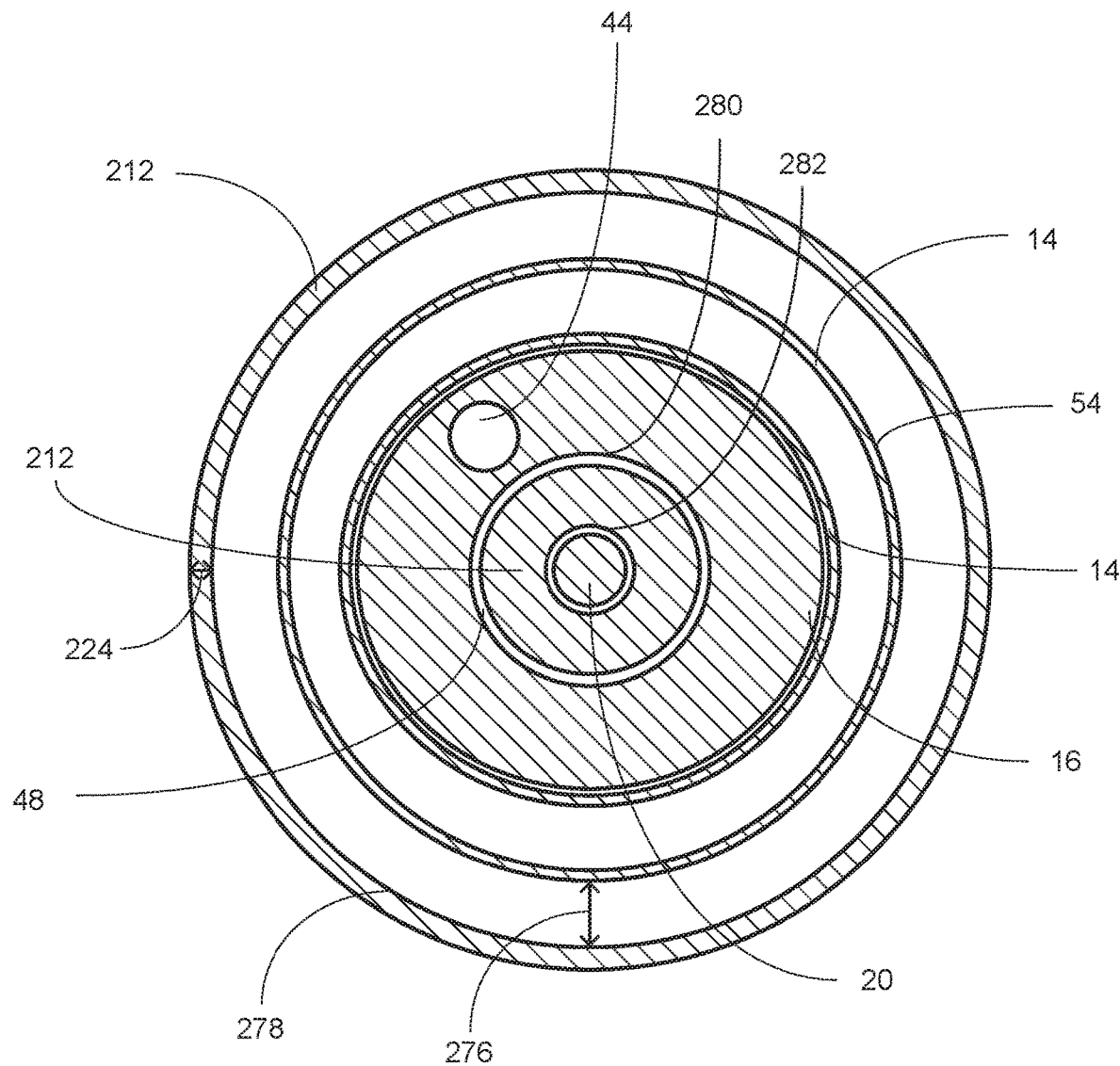
FIG. 7 is a conceptual and schematic diagram illustrating a cross-sectional view of the distal portion of the medical device of FIG. 6.

FIG. 7 is a conceptual and schematic diagram illustrating a cross-sectional view along the longitudinal axis 228 of the sheath 212 as viewed at the cross-sectional plane 232 in FIG. 6. The sheath 212 fully encircles the expandable balloon 14. The sheath 212 may define a relatively consistent wall thickness 224. In some examples, the wall thickness 224 may be consistent throughout the circumference of the sheath 212 (e.g., as depicted in FIG. 7) as well as throughout the length of the sheath 212. In other examples, the wall thickness 224 may vary along the length of the sheath 212, and may be consistent or vary throughout the circumference of the sheath 212.

In some examples, when in the deployed configuration 262 the sheath 212 defines a space 276 between an inner wall 278 of the sheath 212 and an outer surface 54 of the expandable balloon 14. As discussed herein, in other examples the sheath 212 contacts the expandable balloon 14 as the expandable balloon 14 is navigated to the target site 70 in the deployed configuration 262. In some examples, configuring the sheath 212 to contact the outer surface 54 of the expandable balloon 14 in the deployed configuration 262 may reduce the profile of the distal portion of the medical device 10, enabling the expandable balloon 14 to be navigated through relatively more tortuous or constricted vasculature 24 than a medical device 10 with a larger profile. The sheath 212 may be configured to avoid applying a substantial inward radial force, as inward radial forces may increase the chance of damaging the integrity of the expandable balloon 14, the integrity of any drug coated on the outer surface 54 of the expandable balloon 14, or both.

In some examples, to facilitate the independent axial movement of the guidewire 20 and sheath 12, both an inner wall 280 of the shared lumen 48 and an inner wall 282 of the sheath 212 may be treated or coated to be lubricious. The inner walls 280, 282 of the shared lumen 48 and sheath 212 may be treated or coated with any of the lubricious materials described herein. Configuring both inner walls 280, 282 to be lubricious may provide advantages by potentially reducing the friction and therein increasing the control of axial movement of both the catheter 16 moving over the guidewire 20 and the sheath 212 moving within the catheter 16.

Figure 8:
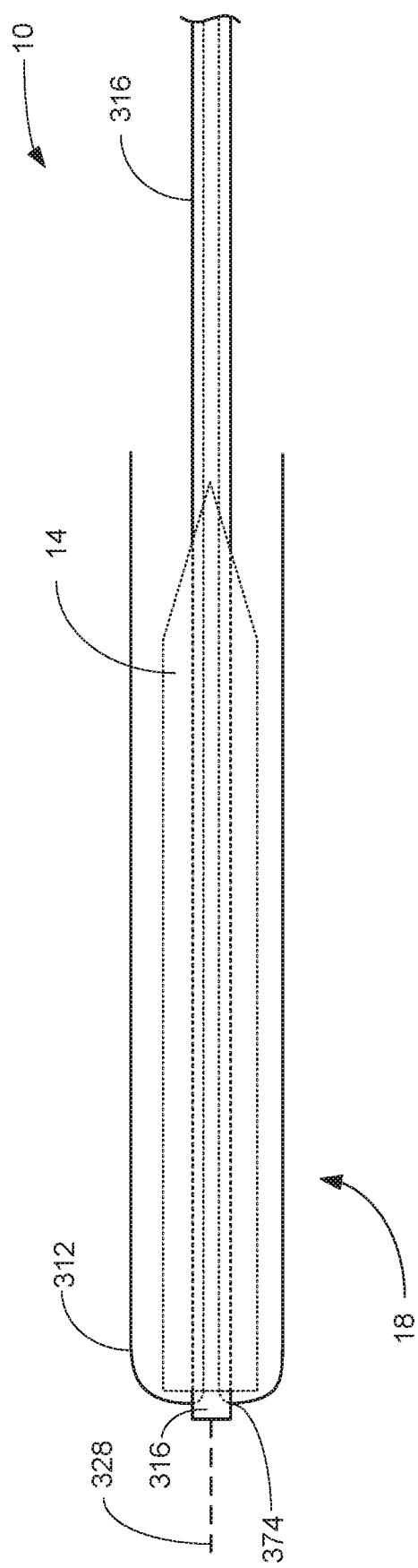
FIG. 8 is a conceptual and schematic diagram illustrating a side view of another example sheath enclosing an expandable balloon at the distal portion of a medical device.

In some examples, a sheath is configured to only extend radially from the catheter 16 (e.g., not distally) to enclose the expandable balloon 14. For example, FIG. 8 is a conceptual and schematic diagram illustrating an example sheath 312 that is enclosing an expandable balloon 14 on the distal portion 18 of a catheter 316 on a medical device 10. The sheath 312 may be substantially similar to the sheaths 12, 112, 212 of FIGS. 1A-7 aside from any differences described herein. Further, the catheter 316 may be substantially similar to the catheter 16 of FIGS. 1A-7 aside from any differences described herein. The catheter 316 extends distally beyond the expandable balloon 14. The sheath 312 extends radially out from a location 374 on the catheter 316 that is distal to the expandable balloon 14. After extending radially outwards, the sheath 312 extends proximally to enclose the expandable balloon 14. The sheath 312 may extend back substantially parallel to a longitudinal axis 328 of the medical device 10. Configuring the catheter 316 such that the sheath 312 extends from a location 374 radially outward and proximally (e.g., but not distally) to enclose the expandable balloon 14 may simplify the mechanical operation of the medical device 10, potentially reducing stresses upon the sheath 312 and therein potentially decreasing a chance for structural failure.

Figure 9:
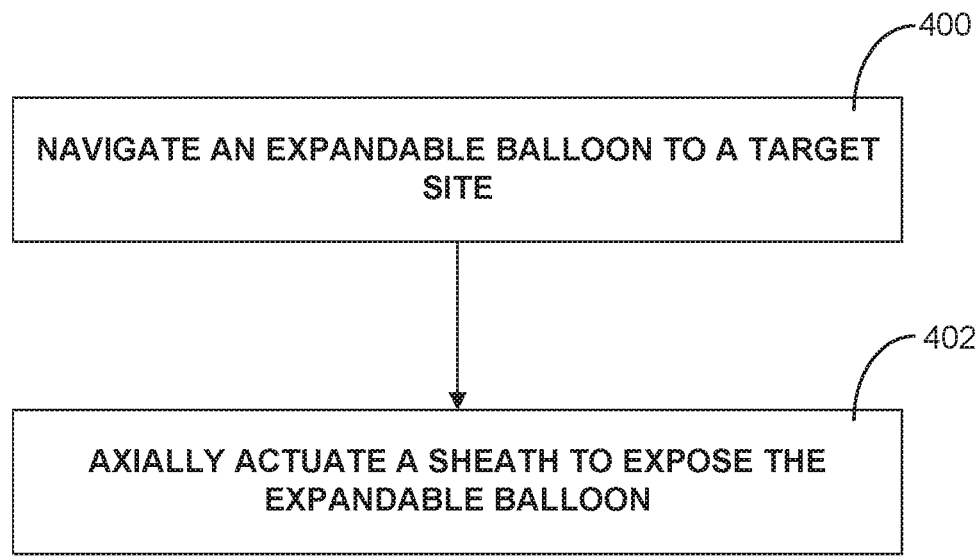
FIG. 9 is a flow diagram illustrating a method of navigating an expandable balloon to a target site within a patient while the expandable balloon is enclosed within a sheath.

FIG. 9 is a flow diagram illustrating a method of deploying expandable balloons 14. Though the method of deploying expandable balloons 14 is discussed primarily with reference to the systems and devices of FIGS. 1A-4B, it is to be understood that this method may be executed using any of the systems and devices described herein. A clinician may navigate an expandable balloon 14 to a target site 70 (400). The target site 70 may be within the vasculature 24 of a patient 26. The clinician may navigate the expandable balloon 14 to the target site 70 using a medical device 10. The medical device 10 includes a catheter 16. The expandable balloon 14 may be on a distal portion 18 of the medical device 10 and may be enclosed by a sheath 12 that is in a deployed configuration 62 (e.g., the sheath 12 extending proximally from a distal opening 60 of a sheath lumen 46 at a distal end 58 of the catheter 16 to a location that is proximal to the expandable balloon 14).

In some examples, the sheath 12 encloses the expandable balloon 14 in the deployed configuration 62 while the medical device is retracting proximally from the vasculature 24 of the patient 26. During a clinical operation, a clinician may want to partially or fully retract the distal portion 18 of the medical device 10 from the vasculature of a patient 26 due to a development or complication. The sheath 12 may remain in the deployed configuration 62 and enclose (and therein protect the integrity of) the expandable balloon 14 during this process. In some examples, the sheath 12 enables the clinician to retract the catheter 16 as a result of a distal end 220 of the sheath 12 being configured to affix to an external surface 222 of the catheter (e.g., similar to the distal end 220 of the sheath 212).

Once the clinician navigates the expandable balloon 14 to the target site 70, the clinician actuates the sheath 12 to the retracted configuration 96 to expose the expandable balloon 14 (402). Upon the clinician exposing the expandable balloon 14, the clinician may inflate the expandable balloon 14 to the inflated state 100. The clinician inflates the expandable balloon 14 using the inflation lumen 44. After inflating the expandable balloon 14, the clinician deflates the expandable balloon 14. The clinician may deflate the expandable balloon 14 again using the inflation lumen 44. The clinician may deflate the expandable balloon 14 to a variant of the deflated configuration 52 (e.g., a profile that is relatively larger than the deflated configuration 52 as it may be difficult for the inflation lumen 44 to deflate the expandable balloon 14 to the precise folded and/or pleated state of the expandable balloon 14 prior to inflation).

In some examples, the clinician deflates the expandable balloon 14 in response to the expiration of a time threshold (e.g., an amount of time in which the drug on the outer surface 54 of the expandable balloon 14 has been sufficiently applied to the target site 70). Once the clinician deflates the expandable balloon 14, the clinician may re-deploy the sheath 12 to the deployed configuration 62 to re-enclose the expandable balloon 14. The clinician retracts the medical device 10 proximally to remove the medical device 10 from the patient 26.

In some examples, the clinician may retract the sheath 12 by proximally retracting the sheath 12 through the catheter 16. The clinician may proximally retract the sheath 12 by applying a proximal force to a proximal portion 40 of the sheath 12. As a result of the clinician proximally retracting the proximal portion 40 of the sheath 12 through the catheter 16, the distal portion 72 of the sheath 12 may retract distally to the location 74 where the sheath 12 enters the catheter 16. Upon entering the catheter 16, the distal portion 72 of the sheath 12 may continue moving proximally (e.g., if the proximal force is still applied to the proximal portion 40 of the sheath 12).

Alternatively, the clinician may retract the sheath 12 by distally moving the sheath 12 through the catheter 16. The clinician may distally retract the sheath 12 by applying a distal force to a proximal portion 40 of the sheath 12. In response to the distal force, the sheath 12 may be configured to distally move past the expandable balloon 14.

Various examples of the disclosure have been described. These and other examples are within the scope of the following claims.

What is claimed is:

1. A medical device comprising:
a catheter comprising a catheter shaft comprising a proximal end and a distal end, wherein the catheter shaft defines a sheath lumen having a distal opening at or near the distal end of the catheter;
an expandable balloon mounted in a deflated state on a portion of the catheter proximate to the distal end of the catheter at a location proximal to the distal opening of the sheath lumen; and
a sheath configured to move from a deployed configuration wherein the sheath extends from the distal opening of the sheath lumen past a distal end of the expandable balloon and proximally over an outer surface of the expandable balloon, to a retracted configuration wherein the sheath moves axially within the sheath lumen to expose the outer surface of the expandable balloon, wherein the sheath includes a distal portion that is configured to be flexible and a proximal portion that is configured to have a relatively high tensile strength.

2. The medical device of claim 1, wherein the sheath is configured to extend proximally over the outer surface of the expandable balloon to a location proximal to the expandable balloon.

3. The medical device of claim 1, wherein the sheath is configured to retract proximally within the sheath lumen to expose the outer surface of the expandable balloon.

4. The medical device of claim 1, wherein the sheath is configured to move distally past the distal end of the expandable balloon to expose the expandable balloon.

5. The medical device of claim 4, wherein the sheath includes a hypotube.

6. The medical device of claim 1, wherein the sheath is configured to shield the outer surface of the expandable balloon from a vasculature of a patient as the expandable balloon is navigated to a target site in the patient.

7. The medical device of claim 6, wherein the sheath is configured to be actuated from the deployed configuration to the retracted configuration after navigating the expandable balloon to the target site.

8. The medical device of claim 6, wherein the sheath is configured to shield the expandable balloon from the vasculature of the patient as the expandable balloon is removed proximally from the body of the patient.

9. The medical device of claim 1, wherein the catheter further comprises an inflation lumen fluidly connected to an internal volume of the expandable balloon to enable inflation of the expandable balloon.

10. The medical device of claim 1, wherein the catheter further comprises a guidewire lumen.

11. The medical device of claim 10, wherein the guidewire lumen is parallel with the sheath lumen.

12. The medical device of claim 10, wherein the sheath lumen is coaxial with the guidewire lumen of the catheter.

13. The medical device of claim 1, wherein the sheath extends distally from the distal opening.

14. The medical device of claim 1, wherein a distal portion of the sheath is configured to be secured to an external surface of the catheter proximal to the expandable balloon.

15. The medical device of claim 14, wherein the distal portion of the sheath is configured to be detached from the external surface in response to the sheath being retracted proximally through the sheath lumen.

16. The medical device of claim 1, wherein an outer surface of the expandable balloon is coated with a drug.

17. The medical device of claim 1, wherein an outer surface of a distal portion of the sheath when in the deployed configuration is coated with a drug.

18. The medical device of claim 17, wherein the expandable balloon is coated with the drug.

19. The medical device of claim 17, wherein the expandable balloon is coated with a different drug.

20. The medical device of claim 1, wherein an outer surface of a distal portion of the sheath when in the deployed configuration is coated with a lubricious coating.

21. The medical device of claim 1, wherein the sheath comprises at least one of polytetrafluoroethylene, polyethylene, a biodegradable polymer, a flexible plastic blends or a thin-walled metal alloy.

22. A method of deploying expandable balloons, the method comprising:
navigating a distal portion of a catheter of a medical device through vasculature of a patient to a target site within the patient, the medical device comprising:
a catheter with a catheter shaft that defines a sheath lumen, wherein the sheath lumen terminates distally with a distal opening at or near a distal end of the catheter,
an expandable balloon mounted in a deflated state on the distal portion of the catheter at a location proximal to the distal opening of the sheath lumen, and
a sheath configured to move from a deployed configuration wherein the sheath extends proximally from the distal opening of the sheath lumen to substantially cover the expandable balloon, to a retracted configuration wherein the sheath moves axially through the sheath lumen to expose the expandable balloon after navigating the distal portion of the catheter to the target site, wherein the sheath includes a distal portion that is configured to be flexible and a proximal portion that is configured to have a relatively high tensile strength,
actuating the sheath axially through the sheath lumen to expose the expandable balloon to the vasculature of the patient.

23. The method of claim 22, further comprising:
retracting the distal portion of the catheter out of the vasculature of the patient; and
reinserting the distal portion of the catheter into the vasculature of the patient for navigation of the distal portion to the target site.

24. The method of claim 22, wherein moving the sheath from the deployed configuration to the retracted configuration comprises retracting the sheath proximally through the sheath lumen thereby moving the sheath distally from the expandable balloon and then proximally within the sheath lumen.

25. The method of claim 24, wherein retracting the sheath proximally through the sheath lumen comprises proximally pulling on a proximal end of the sheath that extends out from a proximal hole at or near a proximal end of the catheter.

26. The method of claim 22, wherein moving the sheath from the deployed configuration to the retracted configuration comprises pushing the sheath distally through the sheath lumen thereby moving the sheath distally from the expandable balloon.

27. The method of claim 26, wherein pushing the sheath distally through the sheath lumen comprises distally pushing a proximal end of the sheath that extends out from a proximal hole on a proximal end of the catheter.

28. The method of claim 22, wherein an outer surface of the expandable balloon is coated with a drug, the method further comprising inflating the expandable balloon through an inflation lumen to press drug-coated walls of the expandable balloon against the target site in response to actuating the sheath axially through the sheath lumen to expose the expandable balloon to the vasculature of the patient.

29. The method of claim 28, further comprising deflating the expandable balloon after a threshold period of time has elapsed since the drug-coated walls of the expandable balloon pressed against the target site as a result of inflating the expandable balloon.

30. The method of claim 29, further comprising:
actuating the sheath axially through the sheath lumen to re-cover the expandable balloon subsequent to deflating the expandable balloon; and
retracting the catheter out of the vasculature of the patient.

31. A medical device comprising:
a catheter comprising a catheter shaft comprising a guidewire lumen, an inflation lumen, and a sheath lumen that all extend throughout a length of the catheter, the sheath lumen terminating distally with a distal opening at or near a distal end of the catheter;
wherein the catheter is configured to follow a guidewire with the guidewire lumen sliding along the guidewire;
an expandable balloon mounted in a deflated state on the distal portion of the catheter at a location proximal to the distal opening of the sheath lumen, wherein the inflation lumen is configured to both inflate and deflate the expandable balloon; and
a sheath configured to move from a deployed configuration wherein the sheath extends distally from the distal opening of the sheath lumen to extend proximally to substantially cover the expandable balloon, to a retracted configuration wherein the sheath moves axially within the sheath lumen to expose the outer surface of the drug-coated balloon, wherein the sheath includes a distal portion that is configured to be flexible and a proximal portion that is configured to have a relatively high tensile strength.

* * * * *